United States Patent [19]
Reiter et al.

[11] 3,992,363
[45] Nov. 16, 1976

[54] PHOTOPOLYMERIZATION INITIATORS

[75] Inventors: Ralph H. Reiter; George Rosen, both of Wayne, N.J.

[73] Assignee: Sun Chemical Corporation, New York, N.Y.

[22] Filed: Nov. 18, 1974

[21] Appl. No.: 524,971

Related U.S. Application Data

[62] Division of Ser. No. 455,667, March 28, 1974, Pat. No. 3,929,490.

[52] U.S. Cl. ............................ 526/292; 204/159.17; 204/159.23; 260/2 R; 526/293
[51] Int. Cl.² ...................... C08F 8/18; C08F 12/12; C08G 61/10
[58] Field of Search ............................... 260/93.5 A

[56] References Cited
UNITED STATES PATENTS

| | | | |
|---|---|---|---|
| 3,219,644 | 11/1965 | Leavitt .......................... | 260/93.5 A |
| 3,525,713 | 8/1970 | Bloch et al. .................... | 260/93.5 A |

*Primary Examiner*—Wilbert J. Briggs, Sr.
*Attorney, Agent, or Firm*—Cynthia Berlow

[57] ABSTRACT

Ethylenically unsaturated monomers in the presence of a novel aromatic oligomeric compound or polymer having a polyhaloacetyl moiety attached thereto are polymerized upon exposure to a source of radiation.

2 Claims, No Drawings

PHOTOPOLYMERIZATION INITIATORS

This is a division of application Ser. No. 455,667, filed Mar. 28, 1974, now U.S. Pat. No. 3,929,490.

This invention relates to photopolymerization initiators. More particularly it relates to novel polyhaloacyl aromatic compounds as photoinitiators for ethylenically unsaturated monomeric compounds.

The use of photopolymerizable ethylenically unsaturated monomeric materials in coating compositions, printing inks, adhesives, and the like is known. It is also known that such monomeric materials are converted into polymers by the action of radiation and that they will polymerize at an improved rate when exposed to radiation in the presence of a photoinitiator.

The use of such photopolymerizable compositions in inks, coatings, adhesives, and presensitized photopolymeric printing plates has been described in, for example, U.S. Pat. Nos. 3,551,235; 3,551,246; 3,551,311; 3,552,387; and 3,759,809.

The initiators of this invention are polyhaloacyl aromatic compounds which may be prepared by any known and convenient method, such as for example by (1) a two-step process comprising (a) reacting a suitable starting aromatic compound with an acylating agent such as an acyl halide, acid anhydride, or carboxylic acid to form its acyl derivative and then (b) halogenating the acyl derivative to obtain the desired polyhaloacyl aromatic compound or by (2) a one-step process comprising reacting the starting aromatic compound with a polyhalogenated acylating agent such as polyhaloacyl halide, a polyhalo acid anhydride, or a polyhalogenated carboxylic acid.

The preparation of the compounds of this invention will be illustrated as follows with poly($\alpha$-methylstyrene) as the starting material and poly(p-trihaloacetyl-$\alpha$-methylstyrene) as the product; it is not, however, intended to be limited thereto:

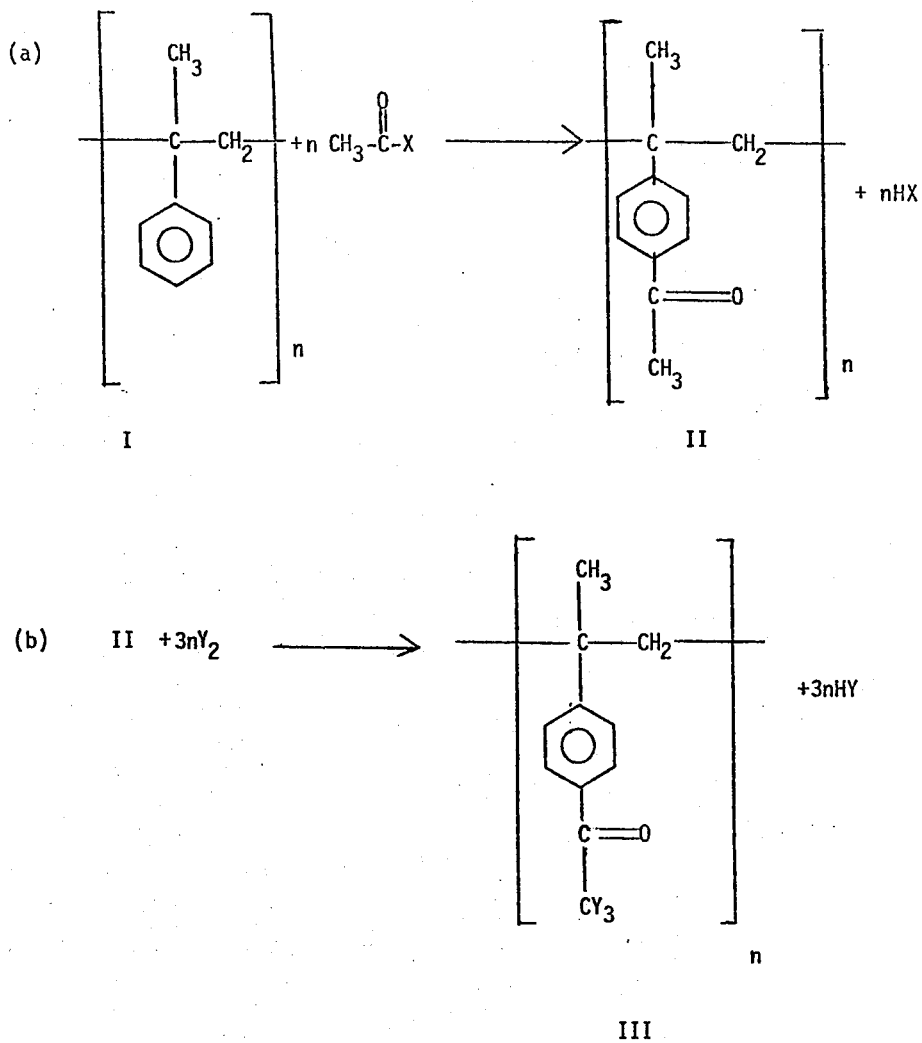

It has now been found that certain polyhaloacyl aromatic oligomers and higher polymers are effective initiators for the photopolymerization of ethylenically unsaturated compounds.

wherein $n$ is an integer of 2 to about 100 and X and Y is each chlorine, bromine, iodine, or fluorine and may be the same or different.

Other procedures by which the intermediate acetyl derivative can be made include, for example, 1. the preparation of the alcohol from a poly(haloaromatic) compound and a cetaldehyde via the Grignard reaction, followed by oxidation:

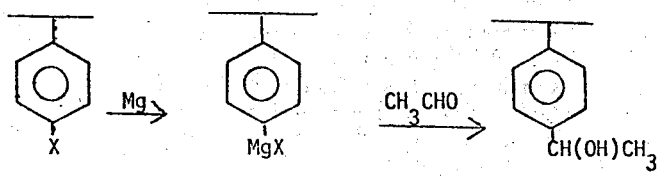

wherein X is chlorine, bromine, or iodine (2) oxidation of a poly(ethylaromatic) compound

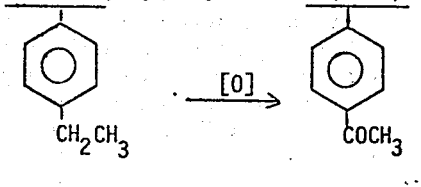

(3) reaction of a poly(aromatic acid) with a metal alkyl

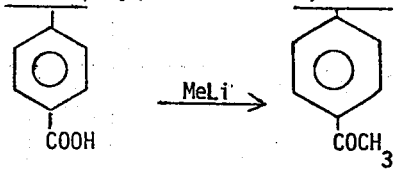

The starting material I may be poly(α-methylstyrene) as shown above; other suitable polyaromatic starting materials include, but are not limited to, biphenyl, terphenyls, and poly(phenylenes); diphenyl oxide poly(phenylene oxides); poly(benzyl) and poly(phenylglycidyl ethers): poly(styrene oxides); poly(styrene), poly(vinyltoluene), and copolymers thereof; poly(phenylvinyl ethers); poly(phenylacrylates); poly(phenylmethacrylates), poly(substituted phenylacrylates), poly(substituted phenylmethacrylates); di- and triphenylmethane and compounds containing the di- or triphenylmethane structure, such as poly(xylylenes) and triphenylmethane dyes; coumarone-indene resins; naphthalene, phenanthrene, anthracene, and other condensed ring compounds and compositions containing the condensed ring structure; and the like; and their mixtures.

The acetyl halide of reaction step (a) may be the chloride, bromide, iodide, or fluoride, and the halogen of reaction step (b) may be chlorine, bromine, iodine, or fluorine.

Reaction (a) generally takes place within the temperature range of about −40° to 120° C., and preferably about −10° to 5° C. Reaction (b) takes place within the temperature range of about 0° to 120° C., and preferably about 20° to 100° C. Each reaction takes place in the presence of a suitable solvent, e.g., tetrachloroethane, dichloroethane, chloroform, a nitrohydrocarbon, carbon disulfide, carbon tetrachloride, and the like, in the presence or absence of a suitable catalyst, e.g., aluminum chloride; ferric chloride; zinc chloride; iodine; an inorganic acid, e.g., sulfuric, hydrochloric, or polyphosphoric acid; and the like.

When a one-step reaction is employed, the starting polyaromatic compound may be one of those listed above. When the reactant is an acyl halide, it has the formula

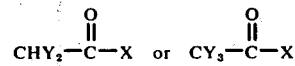

where X and Y is each chlorine, bromine, iodine, or fluorine and may be the same or different. Examples of suitable polyhaloacyl halides include, but are not limited to, trichloroacetyl chloride, trichloroacetyl bromide, tribromoacetyl chloride, dichloroacetyl chloride, trifluoroacetyl chloride, perfluoroalkyl chloride, perchloroalkyl chloride, perbromoalkyl chloride, periodoalkyl chloride, and the like.

Examples of the compounds of this invention include, but are not limited to, poly(dichloroacetyl-α-methylstyrene), poly(dibromoacetyl-α-methylstyrene), poly(trichloroacetyl-α-methylstyrene), poly(tribromoacetylstyrene), poly(diiodoacetylstyrene), poly(trichloroacetylstyrene), poly(trichloroacetylphenyl oxide), poly(trichloroacetylphenyl glycidyl ether), poly(trichloroacetylvinyltoluene), poly(p-trichloroacetylphenyl acrylate), poly(trichloroacetylbenzyl), and trichloroacetyl-p-terphenyl.

The photoinitiators of this invention may be used with any polymerizable ethylenically unsaturated compound which has at least one $CH_2=C<$, $-CH=CH-$, $-CH=C<$, or $>C=C<$ group per molecule, such as for example acrylates, methacrylates, maleates or itaconates of monohydric alcohols or polyhydric alcohols, e.g., methyl alcohol, ethyl alcohol, butyl alcohol, hexyl alcohol, 2-ethylhexyl alcohol, lauryl alcohol, dimethylaminoethyl alcohol, hydroxyethyl alcohol, 2-methoxyethyl alcohol, ethylene glycol, triethylene glycol, tetraethylene glycol, neopentyl glycol, 1,10-decanediol, trimethylolethane, trimethylolpropane, butanediols, pentaerythritol, dipentaerythritol, tripentaerythritol, other polypentaerythritols, sorbitol, d-mannitol, and the like, modified acrylates, methacrylates, maleates, and itaconates; acrylated, methacrylated, maleated, and itaconated prepolymers, e.g., epoxy resins, oil and oil-free alkyd resins, urethanes, linear polyesters; vinyl ethers such as vinyl ethyl ether, vinyl butyl ether, hydroxyethyl vinyl ether, aminopropyl vinyl ether, dimethylaminoethyl vinyl ether, and vinyloxypropoxyethanol; vinyloxyalkyl esters such as vinyloxethyl acetate; methacrylonitrile or acrylonitrile; acrylamide or methacrylamide and their N-substituted derivatives; vinyl esters such as vinyl chloride, vinyl bromide, vinyl acetate, vinyl butyrate, vinyl propionate, and vinyl stearate; vinylidene esters such as vinylidene chloride, vinylidene fluoride, and vinylidene cyanide; styrene; substituted styrenes such as methylstyrene, dimethylstyrene, and halogenated styrenes; vinyl ketones such as methyl vinyl ketone, ethyl vinyl ketone, and vinyl phenyl ketone; and the like, and mixtures thereof.

The ratio of the amount of monomeric compound to the amount of initiator is about 50 to 99: 1 to 50, and preferably about 94 to 99: 1 to 6.

Commonly known modifiers may be incorporated into the formulations using these compositions, including plasticizers; colorants; wetting agents for the colorant, such as dichloromethylstearate and other chlorinated fatty esters; leveling agents, such as lanolin, paraffin waxes, and natural waxes; and the like. Such modifiers are generally used in amounts ranging up to about 3 percent by weight, preferably about 1 percent, based on the total weight of the formulation. The formulations may be prepared in any known and convenient manner.

Variables which determine the rate at which photopolymerizable composition will dry include the nature of the substrate, the specific ingredients in the composition, the concentration of the photoinitiator, the thickness of the material, the nature and intensity of the radiation source and its distance from the material, the presence or absence of oxygen, and the temperature of the surrounding atmosphere. Irradiation may be accomplished by any one or a combination of a variety of methods. The composition may be exposed, for example, to actinic light from any source and of any type as long as it furnishes an effective amount of ultraviolet radiation, since the compositions activatable by actinic light generally exhibit their maximum sensitivity in the range of about 180nm to 400nm, and preferably about 200nm to 300 nm; electron beams; gamma radiation emitters; and the like; and combinations of these. Suitable sources include, but are not limited to, carbon arcs, mercury vapor arcs, pulsed xenon lamps, fluorescent lamps with special ultraviolet light-emitting phosphors, argon glow lamps, photographic flood lamps, Van der Graaff accelerators, and so forth.

The time of irradiation must be sufficient to give the effective dosage. Irradiation may be carried out at any convenient temperature, and most suitably is carried out at room temperature for practical reasons. Distances of the radiation source from the work may range from about 0.1 inch to 6 feet, and preferably about 0.1–6 inches.

When cured by radiation, the compositions are dry, flexible, abrasion resistant, and chemical resistant; also they have excellent ink receptivity, hydrophilic-hydrophobic balance, dot resolution, and initial roll-up, making them particularly suitable in such applications as presensitized lithographic printing plates and photoresists. The compositions are also useful as printing inks, adhesives for foils, films, papers, fabrics, and the like; coatings for metals, plastics, paper, wood, foils, textiles, glass, cardboard, box board, and the like; markers for roads, parking lots, airfields, and similar surfaces; and so forth.

When used as vehicles for inks, e.g., printing inks, the compositions may be pigmented with any of a variety of conventional organic or inorganic pigments, e.g., molybdate orange, titanium white, chrome yellow, phthalocyanine blue, and carbon black, as well as colored with dyes in a conventional amount. For example, the vehicle may be used in an amount ranging from about 20 to 99.9 percent and the amount of colorant may range from about 0.1 to 80 percent of the weight of the total composition.

Stock which may be printed includes paper, clay-coated paper, and box board. In addition, the compositions are suitable for the treatment of textiles, both natural and synthetic, e.g., in vehicles for textile printing inks or for specialized treatments of fabrics to produce water repellency, oil and stain resistance, crease resistance, etc.

When the photopolymerizable materials are used as adhesives, at least one of the substrates must be translucent or transparent when ultraviolet light is used. When the radiation source is an electron beam or gamma radiation, at least one of the substrates must be capable of transmitting high energy electrons or gamma radiation, respectively, and neither is necessarily translucent to light. Typical laminations include polymer-coated cellophane to polymer-coated cellophane films, polymer-coated cellophane film to polypropylene, Mylar to a metal substance such as aluminum or copper, polypropylene to aluminum, and the like.

The photopolymerizable compositions may be utilized for metal coatings and particularly for metals which are to be subsequently printed. Glass and plastics may also be printed or coated, and the coatings are conventionally applied by roller or spray. Pigmented coatings systems may be used for various polyester and vinyl films; glass; polymer-coated cellophane; treated and untreated polyethylene, for example in the form of disposable cups or bottles; treated and untreated polypropylene; and the like. Examples of metals which may be coated include sized and unsized tin plate.

Photopolymerizable elements prepared from the materials comprise a support, e.g., a sheet or plate, having superimposed thereon a layer of the above-described photopolymerizable material. Suitable base or support materials include metals, e.g., steel and aluminum plates; sheets; and foils; and films or plates composed or various film-forming synthetic resins or high polymers, such as addition polymers, and in particular vinyl polymers, e.g., vinyl chloride polymers; vinylidene chloride polymers; vinylidene chloride copolymers with vinyl chloride, vinyl acetate, or acrylonitrile; and vinyl chloride copolymers with vinyl acetate or acrylonitrile; linear condensation polymers such as a polyester, e.g., polyethylene terephthalate; polyamides; etc. Fillers or reinforcing agents can be present in the synthetic resin or polymer bases. In addition, highly reflective bases may be treated to absorb ultraviolet light, or a light absorbtive layer can be transposed between the base and photopolymerizable layer.

Photopolymerizable elements can be made by exposing to radiation selected portions of the photopolymerizable layer thereof until addition polymerization is completed to the desired depth in the exposed portions. The unexposed portions of the layer are then removed, e.g., by the use of solvents which dissolve the monomer or prepolymer but not the polymer.

When used as printing inks, coating compositions, and adhesives, the compositions as described herein are used without volatile solvents and possess many advantages over conventional oleoresinous and solvent-type inks and coatings. The substrate need not be pretreated or prepared in any way. The use of volatile solvents and the attendant hazards and air pollution are eliminated. The inks and coating have excellent adhesion to the substrate after exposure to radiation. They have good gloss and rub-resistance and withstand temperatures as high as about 150° C. and as low as about −20° C. The printed or coated sheets can be worked and turned immediately after exposure to the energy source.

The invention and its advantages will be better understood with reference to the following illustrative examples, but it is not intended to be limited thereto. In the examples, the parts are given by weight unless otherwise specified. Unless otherwise indicated, when the ingredient is solid at room temperature, the mixture may be heated to melt the solid ingredient, but generally not above 100° C., or it may be used in a mixture with other liquid ingredients. The atmospheric and temperature conditions were ambient unless otherwise noted.

EXAMPLE 1

A. To a flame-dried one-liter flask equipped with a stirrer, drying tube, addition funnel, and thermometer was charged 251 grams of aluminum chloride and 250 ml. of carbon disulfide. Over a period of 80 minutes were added a solution of 218 grams of poly($\alpha$-methylstyrene), available as Dow Resin 276-V2 from the Dow Chemical Company, in 158 grams of acetyl chloride while maintaining the temperature at −5° to 5° C. The mixture was allowed to warm to 15° C. over 40 minutes and then discharged into an ice-HCl mixture, washed until neutral, and taken up in benzene/methylethyl ketone. Residual water was removed azeotropically. The product was vacuum-stripped to yield 230 grams (77.5%) of a dark amber liquid having a Gardner viscosity of Z9-Z10 (855-1066 poise).

| Analysis: | Theoretical | 10.00 % 0 |
|---|---|---|
| | Found | 10.40 % 0 |

Its infra-red spectrum showed a carbonyl absorption at 5.97 microns.

B. A solution of 140 grams of the product of part (A) in 140 ml. of benzene and 375 ml. of acetic acid was charged to a one-liter flask fitted with a gas inlet tube, condenser, stirrer, and thermometer. Chlorine gas (238 grams) was added over one hour. The temperature was allowed to rise to 60° C. and held until the reaction mixture showed a strong yellow-green color. Residual chlorine was swept out with nitrogen for one hour, and 225 grams of anhydrous sodium acetate was added. The temperature was raised to 95° C., and chlorine gas added at about half the previous rate. The temperature was held at 95°-99° C. for one hour at which time 112 grams of chlorine had been charged. Nitrogen was sparged through the mixture for 40 minutes while a temperature of 90° C. was maintained. After cooling to 70°-75° C., the reaction mixture was poured with stirring into 18 grams of sodium sulfite dissolved in a mixture of 1425 grams of water and 625 grams of ice. After allowing the mixture to warm to room temperature, the lower organic layer was withdrawn and stripped under aspirator vacuum at 100° C. for two hours. A yield of 232 grams of a dark brown tarry solid, poly(trichloroacetyl-$\alpha$-methylstyrene) (PolyTCAP), was obtained, representing a weight gain corresponding to the reaction of 3.03 gram-atoms of chlorine per equivalent of aromatic ring.

| Analysis of $C_{11}H_9OCl_3$: | Theoretical | 40.5 % | Cl |
|---|---|---|---|
| | Found | 42.05 % | Cl |

Its infra-red spectrum showed a carboxyl absorption at 5.87 microns.

The product was non-lachrymatory and had little odor.

EXAMPLE 2

The use of $\alpha,\alpha$-dichloroacetophenone (DCAP) and $\alpha,\alpha,\alpha$-trichloroacetophenone (TCAP) as photoinitiators is known. These compounds, however, have limited commercial applicability. Because of its lachrymatory properties, the dichloro compound is unsuitable for use in inks and coatings. The trichloro compound is less irritating than the dichloro compound but it is somewhat irritating and has an offensive odor, precluding its use in inks and other thin-film applications. A comparison of the properties of these compounds and a product of this invention (PolyTCAP, prepared in Example 1) has been made.

(A) One gram each of TCAP and PolyTCAP was placed on a watch crystal and kept in an oven at 50° C. for 72 hours. The weight losses, due to evaporation, were as follows:

| TCAP | 96.4 per cent |
|---|---|
| PolyTCAP | 0.3 per cent |

These data demonstrate the superiority of PolyTCAP over its analog TCAP in lack of volatility.

(B) One gram each of TCP and finely-divided PolyTCAP was suspended and agitated in 100 cc. of neutral distilled water for 18 hours. The aqueous layers were separated from the organic compounds, and the amounts of N/5 NaOH required to neutralize 50 cc. aliquots of the aqueous liquids were measured. The amounts of base to reach a phenolphthalein end point were as follows:

| TCAP | 0.32 ml. |
|---|---|
| PolyTCAP | 0.03 ml. |

These data illustrate the superiority of PolyTCAP over its analog TCAP in resistance to hydrolysis.

(C) To demonstrate the relative cure speeds of mixtures of ethylenically unsaturated monomeric materials with DCAP, TCAP, and PolyTCAP as the initiators, runs were made with a variety of monomers with (a) no initiator, (b) DCAP, (c) TCAP, and (d) PolyTCAP; in (b), (c), and (d) the ratio of monomer:initiator was 90:10, except where additionally indicated for the isocyanate-modified pentaerythritol triacrylate. The compositions were exposed at a distance of 3 inches from a 200-watt/inch ultraviolet lamp.

TABLE

| Monomer | no initiator (a) | Cure speeds, seconds DCAP (b) | TCAP (c) | PolyTCAP (d) |
|---|---|---|---|---|
| Pentaerythritol tetraacrylate | 40 | — | 0.5 | 0.2 |
| Trimethylolpropane triacrylate | 90 | — | 5 | 3 |
| Isocyanate-modified pentaerythritol triacrylate (as disclosed in U.S. Pat. No. 3,759,809) | 28 | 2.3 | 0.7–0.8 | 0.5–0.6 |
| + 3 % initiator | | 3.5 | 1.4–1.8 | 1.5–1.6 |
| + 5 % initiator | | 2.5 | 1.0–1.2 | 1.0–1.1 |
| 1,6-Hexanediol diacrylate | 145 | — | 6 | 4 |
| Ethyl acrylate | 180(evaporates) | — | 45 | 40 |
| Methyl methacrylate | 180(evaporates) | — | 25 | 20 |
| Styrene | 180(evaporates) | — | 30 | 27 |
| Divinyl benzene | 180(evaporates) | — | 45 | 36 |

From these data it can be seen that the compositions containing PolyTCAP as the initiator cure faster than the compositions containing either DCAP or TCAP as the initiator.

EXAMPLE 3

To a flame-dried three-liter flask fitted with a thermometer, stirrer, drying tube, and addition funnel was charged 750 ml. of carbon tetrachloride and 133.3 grams (1 mol) of aluminum chloride. A solution of 118.2 grams (1 equivalent) of poly($\alpha$-methylstyrene), available as Dow Resin 276-V2 from The Dow Chemical Company, in 300 ml. of carbon tetrachloride was added rapidly at 2°–6° C. and held for 15 minutes while the mixtures turned brown.

Trichloroacetyl chloride (181.8 grams, 1 mol) was added at −10° to 5° C. over 50 minutes. The temperature was then raised to 10° C. and held there for 1½ hours. The reaction mixture was then dropped into an ice-HCl mixture, washed, dried over $CaCl_2$, filtered, and vacuum-stripped to remove carbon tetrachloride. The yield of poly(trichloroacetyl-$\alpha$-methylstyrene) was 112.5 grams (45.2%) of a dark brown viscous liquid.

EXAMPLE 4

A. To 200 ml. of benzyl chloride in a flame-dried three-liter flask equipped with a thermometer, stirrer, drying tube, and addition funnel was added 2 ml. of $SnCl_4$, and the mixture allowed to stand overnight. It was then dissolved in dioxane and precipitated into water. A solution of 36 grams of the product, poly(benzyl), in 54 ml. of dichloroethane was added to a solution of 62.3 grams of $AlCl_3$ and 33.3 grams of acetyl chloride in 229 ml. of dichloroethane at −5° to 0° C. and held at that temperature for 3 hours. The mixture was then quenched in an ice-HCl mixture; washed in succession with HCl, $NaHCO_3$, and water; and precipitated into hexane. The product was 22.1 grams of poly(acetylbenzyl).

20.6 grams of the poly(acetylbenzyl) was dissolved in 162 ml. of glacial acetic acid and 100 ml. of dichloroethane. It was sparged with 85 grams of chlorine gas at reflux and then sparged with nitrogen. 58.5 grams of anhydrous sodium acetate was then added, heated to reflux, and sparged with 60 grams of chlorine gas. The mixture was then quenched into water plus $Na_2SO_3$.

The organic layer was washed with water and precipitated into methanol.

The product, poly(trichloroacetylbenzyl), was obtained in a yield of 31.1 grams. It has the nominal structure

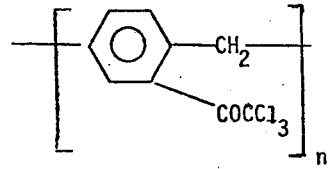

| Analysis: | Theoretical | 45.2 % Cl |
|---|---|---|
| | Actual | 42.9 % Cl |

B. The procedure of Example 2 (C) was repeated with a mixture of 95% of isocyanate-modified pentaerythritol triacrylate and 5% of the product of part (A). The cure was 0.6 second.

EXAMPLE 5

A. 149.4 grams of $AlCl_3$ and 126 ml. of trichloroacetyl chloride were dissolved in 550 ml. of dichloroethane in a three-liter flask fitted with a thermometer, stirrer, drying tube, and addition funnel. A solution of 100 grams of polystyrene in 40 ml. of dichloroethane was added at −5° to 0° C. The mixture was discharged into an ice-HCl mixture; washed in succession with HCl, $NaHCO_3$, and water; and dried over $Na_2SO_4$. The product was vacuum-stripped to yield 102.8 grams of poly(trichloroacetylstyrene) having the nominal structure

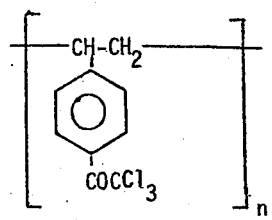

| Analysis: | Theoretical: | 42.7 % Cl |
|---|---|---|
| | Actual: | 16.4 % Cl |

B. The procedure of Example 2 (C) was repeated with a mixture of 95% of isocyanate-modified pentaerythritol triacrylate and 5% of the product of part (A). The cure speed was 2.8 seconds.

EXAMPLE 6

A. To a flame-dried three-liter flask equipped with a stirrer, drying tube, addition funnel, and thermometer was added 22.4 grams of $AlCl_3$ and 12.4 grams of acetyl chloride dissolved in 90 ml. of sym-tetrachloroethane. A solution of 32.2 grams of p-terphenyl in 1600 ml. of sym-tetrachloroethane was added at 0°–5° C. The mixture was then discharged into an ice-HCl mixture and washed in succession with HCl, $Na_2CO_3$, and water. The resulting organic layer was boiled down and 30.1 grams of p-(biphenylyl)acetophenone was obtained, the crude product melting at 227°–232° C.

A mixture of 29.3 grams of the p-(biphenylyl)acetophenone in 1250 ml. of glacial acetic acid was sparged with 21 grams of chlorine gas at 95°–100° C. and then sparged with nitrogen. 16 grams of anhydrous sodium acetate was added, the mixture heated to 93° C., and then sparged with 16 grams of chlorine gas at 93°–97° C. The mixture was discharged into a mixture of water and $Na_2SO_3$. The solvent was removed by boiling and the solid product, p-(biphenylyl)-2,2,2-trichloroacetophenone, was recovered. It has the nominal structure

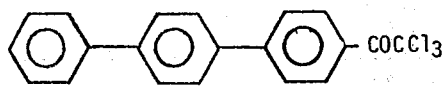

| Analysis: | Theoretical: | 28.3 % Cl |
|---|---|---|
| | Actual: | 30.1 % Cl |

B. The procedure of Example 2 (C) was repeated with a mixture of 95% of isocyanate-modified pentaerythritol triacrylate and 5% of the product of part (A). The cure speed was 1.8 seconds.

EXAMPLE 7

A. To a flame-dried flask equipped with a stirrer, drying tube, addition funnel, and thermometer were charged successively 200.1 grams of $AlCl_3$ in 150 ml. of $CS_2$, 53.3 ml. of acetyl chloride, and 30 grams of mesitylene. The mixture was refluxed for 1 hour and then discharged into an ice-HCl mixture. The $CS_2$ was removed under a vacuum, and the product, diacetylmesitylene, melting at 43.5°–44.5° C. was recrystallized from petroleum ether.

10.2 grams of the diacetylmesitylene and 474 grams of a 5.25% solution of sodium hypochlorite in water were stirred at 55° C. for 7 hours and then at ambient temperature over a weekend. The wet organic cake was recovered by decantation and the product, bis(trichloroacetyl)mesitylene, melting at 95.0°–96.5° C. was recrystallized from ethanol.

B. The procedure of Example 2 (C) was repeated with mixtures of (1) 95% of isocyanate-modified pentaerythritol triacrylate and 5% of the product of part (A) and (2) 90% of isocyanate-modified pentaerythritol triacrylate and 10% of the product of part (A). The cure speeds were 1.7 and 1.0 second, respectively.

EXAMPLE 8

An ink was prepared by grinding on a three-roll mill 85 percent of (1) a composition consisting of 90 percent of pentaerythritol tetraacrylate and 10 percent of PolyTCAP and (2) 15 percent of benzidine yellow. The ink was run on a Miehle press to print coated paper. The printed paper was exposed at a distance of 1¾ inches from two 21-inch 200-watt/inch ultraviolet lamps. The ink dried to a hard, resistant film at a press speed of 350 feet/minute, and had excellent gloss and water-resistance.

EXAMPLE 9

The procedure of Example 8 was repeated with each of the following substrates instead of coated paper: glass, clay-coated sulfite board, untreated aluminum foil and polyolefin film laminated board. The results were comparable.

EXAMPLE 10

A laminate was made of a film of polymer-coated cellophane and a film of oriented polypropylene with a mixture of the following ingredients between the two: 95 parts of trimethylolethane dimethacrylate and 5 parts of poly(trichloroacetyl-α- -methylstyrene).

The laminate was exposed at a distance of 2.0 inches from a 100-watt/inch ultraviolet lamp. A tight bond was effected in 4.0 seconds.

EXAMPLE 11

The procedure of Example 10 was repeated with each of the following substrates: Saran-coated cellophane and Saran-coated cellophane, corona-discharge surface-treated polyethylene and coated cellophane, and polyvinylidene dichloride-coated polypropylene and Mylar.

The laminations were successful as evidenced by tear seals having bond strengths of at least 300 grams per inch.

EXAMPLE 12

The procedures of Examples 2 (C), 4 (B), 5 (B), 6 (B), and 7–11 were repeated except that instead of being exposed to ultraviolet light the samples were passed on a conveyor belt beneath the beam of a Dynacote 300,000-volt linear electron accelerator at a speed and beam current so regulated as to produce a dose rate of 0.5 megarad/second.

These systems produced resinous materials of varying degrees of hardness in films from 0.5 to 20 mils thick having tacky surfaces.

EXAMPLE 13

The procedures of Examples 2 (C), 4 (B), 5 (B), 6 (B), and 7–11 were repeated except that instead of being exposed to ultraviolet light the samples were exposed to a combination of ultraviolet light and electron beam radiation in a variety of arrangements: ultraviolet light, then electron beam; electron beam, then ultraviolet light; ultraviolet light before and after electron beam; electron beam before and after ultraviolet radiation; and simultaneous electron beam and ultraviolet light radiation. The results were comparable.

What is claim is:
1. Poly(trichloroacetyl-α-methylstyrene).
2. Poly(trichloroacetylstyrene).

* * * * *